US00RE42959E

(19) United States
(12) Reissued Patent
Saadat et al.

(10) Patent Number: US RE42,959 E
(45) Date of Reissued Patent: Nov. 22, 2011

(54) APPARATUS AND METHODS FOR STIMULATING REVASCULARIZATION AND/OR TISSUE GROWTH

(75) Inventors: Vahid Saadat, Saratoga, CA (US); John H. Ream, San Jose, CA (US)

(73) Assignee: Abbott Cardiovascular Systems Inc., Santa Clara, CA (US)

(21) Appl. No.: 10/246,030

(22) Filed: Sep. 17, 2002

Related U.S. Patent Documents

Reissue of:
(64) Patent No.: 6,120,520
Issued: Sep. 19, 2000
Appl. No.: 09/271,094
Filed: Mar. 17, 1999

U.S. Applications:
(63) Continuation-in-part of application No. 08/863,791, filed on May 27, 1997, now Pat. No. 5,931,848, and a continuation-in-part of application No. 08/863,877, filed on May 27, 1997, now Pat. No. 5,910,150, and a continuation-in-part of application No. 08/863,925, filed on May 27, 1997, now Pat. No. 5,941,893.

(60) Provisional application No. 60/032,196, filed on Dec. 2, 1996.

(51) Int. Cl.
*A61N 5/06* (2006.01)

(52) U.S. Cl. ..... 606/7; 604/30

(58) Field of Classification Search ..... 606/185, 606/186, 213, 219, 220, 148, 144, 139, 159, 606/170, 7, 15, 10, 46, 1, 14; 604/30, 20; 424/423

See application file for complete search history.

(56) References Cited

U.S. PATENT DOCUMENTS

| | | | |
|---|---|---|---|
| 1,162,901 | A | 12/1915 | Cantry et al. |
| 2,710,000 | A | 6/1955 | Cromer et al. |
| 2,749,909 | A | 6/1956 | Ullery et al. |
| 3,120,845 | A | 2/1964 | Horner |
| 3,470,876 | A | 10/1969 | Barchilon |
| 3,477,423 | A | 11/1969 | Griffith et al. |
| 3,557,794 | A | 1/1971 | Van Patten |
| 3,614,953 | A | 10/1971 | Moss |
| 3,692,020 | A | 9/1972 | Schied |
| 3,780,246 | A | 12/1973 | Beckering et al. |

(Continued)

FOREIGN PATENT DOCUMENTS

EP 0807412 A1 11/1997

(Continued)

OTHER PUBLICATIONS

NASA's Jet Propulsion Laboratory, "Swivel-head Sampling Drill Bit," NASA Tech Briefs, Nov. 1998.

(Continued)

*Primary Examiner* — Kevin T Truong
(74) *Attorney, Agent, or Firm* — Blakely, Sokoloff, Taylor & Zafman LLP; Randy Shen

(57) ABSTRACT

Apparatus and methods for stimulating revascularization and tissue growth are provided using an apparatus having a directable end region carrying a tissue piercing end effector. The apparatus optionally includes electrodes for depositing RF energy to form a controlled degree of scar tissue formation, means for delivering a controlled amount of a bioactive agent at the treatment site, or both.

60 Claims, 5 Drawing Sheets

U.S. PATENT DOCUMENTS

| | | | |
|---|---|---|---|
| 4,207,874 | A | 6/1980 | Choy |
| 4,362,161 | A | 12/1982 | Reimels et al. |
| 4,381,037 | A | 4/1983 | Cuneo |
| 4,461,305 | A | 7/1984 | Cibley |
| 4,468,224 | A | 8/1984 | Enzmann et al. |
| 4,479,896 | A | 10/1984 | Antoniades |
| 4,576,162 | A | 3/1986 | McCorkle |
| 4,578,057 | A | 3/1986 | Sussman |
| 4,582,056 | A | 4/1986 | McCorkle, Jr. |
| 4,600,014 | A | 7/1986 | Beraha |
| 4,640,296 | A | 2/1987 | Schnepp-Pesch et al. |
| 4,646,738 | A | 3/1987 | Trott |
| 4,702,261 | A | 10/1987 | Cornell et al. |
| 4,729,763 | A | 3/1988 | Henrie |
| 4,788,975 | A | 12/1988 | Shturman et al. |
| 4,790,812 | A | 12/1988 | Hawkins, Jr. et al. |
| 4,792,327 | A | 12/1988 | Swartz |
| 4,813,930 | A | 3/1989 | Elliott |
| 4,850,354 | A | 7/1989 | McGurk-Burleson et al. |
| 4,856,529 | A | 8/1989 | Segal |
| 4,895,166 | A | 1/1990 | Farr et al. |
| 4,898,577 | A | 2/1990 | Badger et al. |
| 4,917,102 | A | 4/1990 | Miller et al. |
| 4,923,462 | A | 5/1990 | Stevens |
| RE33,258 | E | 7/1990 | Onik et al. |
| 4,957,742 | A | 9/1990 | Knighton |
| 4,964,854 | A | 10/1990 | Luther |
| 4,976,710 | A | 12/1990 | Mackin |
| 4,985,028 | A | 1/1991 | Isner et al. |
| 5,030,201 | A | 7/1991 | Palestrant |
| 5,087,265 | A | 2/1992 | Summers |
| 5,093,877 | A | 3/1992 | Aita et al. |
| 5,104,393 | A | 4/1992 | Isner et al. |
| 5,106,386 | A | 4/1992 | Isner et al. |
| 5,123,904 | A | 6/1992 | Shimomura et al. |
| 5,125,924 | A | 6/1992 | Rudko |
| 5,125,926 | A | 6/1992 | Rudko |
| 5,133,713 | A | 7/1992 | Huang et al. |
| 5,135,531 | A | 8/1992 | Shiber |
| 5,152,744 | A | 10/1992 | Krause et al. |
| 5,195,988 | A | 3/1993 | Haaga |
| 5,197,968 | A | 3/1993 | Clement |
| 5,224,951 | A | 7/1993 | Freitas |
| 5,242,460 | A | 9/1993 | Klein et al. |
| 5,263,959 | A | 11/1993 | Fischell |
| 5,269,785 | A | 12/1993 | Bonutti |
| 5,273,051 | A | 12/1993 | Wilk |
| 5,281,218 | A | 1/1994 | Irman |
| 5,285,795 | A | 2/1994 | Ryan et al. |
| 5,287,861 | A | 2/1994 | Wilk |
| 5,292,309 | A | 3/1994 | Van Tassel et al. |
| 5,313,949 | A | 5/1994 | Yock et al. |
| 5,323,781 | A | 6/1994 | Ideker et al. |
| 5,324,284 | A | 6/1994 | Imran |
| 5,330,466 | A | 7/1994 | Imran |
| 5,336,237 | A | 8/1994 | Chin et al. |
| 5,339,799 | A | 8/1994 | Kami et al. |
| 5,342,300 | A | 8/1994 | Stefanadis et al. |
| 5,342,393 | A | 8/1994 | Stack |
| 5,354,310 | A | 10/1994 | Garnic |
| 5,358,472 | A | 10/1994 | Vance |
| 5,358,485 | A | 10/1994 | Vance |
| 5,366,468 | A | 11/1994 | Fucci et al. |
| 5,366,490 | A | 11/1994 | Edwards et al. |
| 5,370,675 | A | 12/1994 | Edwards et al. |
| 5,379,772 | A | 1/1995 | Imran |
| 5,380,316 | A | 1/1995 | Aita et al. |
| 5,383,884 | A | 1/1995 | Summers |
| 5,389,073 | A | 2/1995 | Imran |
| 5,389,096 | A | 2/1995 | Aita et al. |
| 5,392,917 | A | 2/1995 | Alpern et al. |
| 5,396,897 | A | 3/1995 | Jain et al. |
| 5,403,334 | A | 4/1995 | Evans et al. |
| 5,409,000 | A | 4/1995 | Imran |
| 5,415,166 | A | 5/1995 | Imran |
| 5,419,777 | A | 5/1995 | Hofling |
| 5,425,376 | A | 6/1995 | Banys et al. |
| 5,429,144 | A | 7/1995 | Wilk |
| 5,439,474 | A | 8/1995 | Li |
| 5,443,443 | A | 8/1995 | Shiber |
| 5,456,689 | A | 10/1995 | Kresch et al. |
| 5,464,395 | A | 11/1995 | Faxon et al. |
| 5,465,717 | A | 11/1995 | Irman et al. |
| 5,488,958 | A | 2/1996 | Topel et al. |
| 5,492,119 | A | 2/1996 | Abrams |
| 5,497,784 | A | 3/1996 | Irman |
| 5,505,725 | A | 4/1996 | Samson |
| 5,507,802 | A | 4/1996 | Irman |
| 5,520,634 | A | 5/1996 | Fox et al. |
| 5,527,279 | A | 6/1996 | Irman |
| 5,531,780 | A | 7/1996 | Vachon |
| 5,551,427 | A | 9/1996 | Altman |
| 5,554,152 | A | 9/1996 | Aita |
| 5,562,694 | A | 10/1996 | Sauer |
| 5,569,178 | A | 10/1996 | Henry |
| 5,569,254 | A | 10/1996 | Carson et al. |
| 5,569,284 | A | 10/1996 | Young et al. |
| 5,575,293 | A | 11/1996 | Miller et al. |
| 5,575,772 | A | 11/1996 | Lennox |
| 5,575,787 | A | 11/1996 | Abela et al. |
| 5,575,810 | A | 11/1996 | Swanson |
| 5,578,067 | A | 11/1996 | Ekwall et al. |
| 5,584,842 | A | 12/1996 | Fogarty et al. |
| 5,588,432 | A | 12/1996 | Crowley |
| 5,591,159 | A | 1/1997 | Taheri |
| 5,593,405 | A | 1/1997 | Osypka |
| 5,601,573 | A | 2/1997 | Fogelbert et al. |
| 5,601,586 | A | 2/1997 | Fucci et al. |
| 5,601,588 | A | 2/1997 | Tonomura et al. |
| 5,606,974 | A | 3/1997 | Castellano et al. |
| 5,607,421 | A | 3/1997 | Jeevanandam et al. |
| 5,609,591 | A | 3/1997 | Daikuzono |
| 5,609,621 | A | 3/1997 | Bonner |
| 5,611,803 | A | 3/1997 | Heaven et al. |
| 5,613,972 | A | 3/1997 | Lee et al. |
| 5,640,955 | A | 6/1997 | Ockuly et al. |
| 5,643,253 | A | 7/1997 | Baxter et al. |
| 5,651,781 | A | 7/1997 | Grace |
| 5,658,263 | A | 8/1997 | Dang et al. |
| 5,662,124 | A | 9/1997 | Wilk |
| 5,662,671 | A | 9/1997 | Barbut et al. |
| 5,665,062 | A | 9/1997 | Houser |
| 5,669,920 | A | 9/1997 | Conley |
| 5,680,860 | A | 10/1997 | Imran |
| 5,683,362 | A | 11/1997 | Rowland et al. |
| 5,688,234 | A | 11/1997 | Frisbie |
| 5,702,412 | A | 12/1997 | Popov et al. |
| 5,709,697 | A | 1/1998 | Ratcliff et al. |
| 5,722,400 | A | 3/1998 | Ockuly et al. |
| 5,724,975 | A | 3/1998 | Negus et al. |
| 5,725,521 | A | 3/1998 | Mueller |
| 5,730,741 | A | 3/1998 | Horzewski et al. |
| 5,743,870 | A | 4/1998 | Edwards |
| 5,755,714 | A | 5/1998 | Murphy-Chutorian |
| 5,766,163 | A | 6/1998 | Mueller et al. |
| 5,776,092 | A | 7/1998 | Farin et al. |
| 5,782,823 | A | 7/1998 | Mueller |
| 5,797,870 | A | 8/1998 | March et al. |
| 5,807,384 | A | 9/1998 | Mueller |
| 5,807,401 | A | 9/1998 | Grieshaber et al. |
| 5,814,028 | A | 9/1998 | Swartz et al. |
| 5,830,210 | A | 11/1998 | Rudko et al. |
| 5,830,222 | A | 11/1998 | Makower |
| 5,833,715 | A | 11/1998 | Vachon et al. |
| 5,834,418 | A | 11/1998 | Brazeau et al. |
| 5,840,059 | A | 11/1998 | March et al. |
| 5,846,225 | A | 12/1998 | Rosengart et al. |
| 5,851,171 | A | 12/1998 | Gasson |
| 5,857,995 | A | 1/1999 | Thomas et al. |
| 5,871,495 | A | 2/1999 | Mueller |
| 5,873,366 | A | 2/1999 | Chim et al. |
| 5,876,373 | A | 3/1999 | Giba et al. |
| 5,878,751 | A | 3/1999 | Hussei et al. |
| 5,885,272 | A | 3/1999 | Aita et al. |
| 5,885,276 | A | 3/1999 | Ammar et al. |
| 5,893,848 | A | 4/1999 | Negus et al. |
| 5,899,874 | A | 5/1999 | Jonsson |

| | | | | |
|---|---|---|---|---|
| 5,906,594 | A | | 5/1999 | Scarfone et al. |
| 5,910,150 | A | | 6/1999 | Saadat |
| 5,916,214 | A | | 6/1999 | Cosio et al. |
| 5,921,982 | A | | 7/1999 | Lesh et al. |
| 5,925,012 | A | * | 7/1999 | Murphy-Chutorian et al. ..... 604/30 |
| 5,928,943 | A | | 7/1999 | Franz et al. |
| 5,931,848 | A | | 8/1999 | Saadat |
| 5,938,632 | A | | 8/1999 | Ellis |
| 5,941,868 | A | | 8/1999 | Kaplan et al. |
| 5,941,893 | A | | 8/1999 | Saadat |
| 5,944,716 | A | | 8/1999 | Hektner |
| 5,951,567 | A | | 9/1999 | Javier, Jr. et al. |
| 5,964,754 | A | | 10/1999 | Osypka |
| 5,964,757 | A | | 10/1999 | Ponzi |
| 5,968,059 | A | | 10/1999 | Ellis et al. |
| 5,971,993 | A | | 10/1999 | Hussein et al. |
| 5,980,545 | A | | 11/1999 | Pacala et al. |
| 5,980,548 | A | * | 11/1999 | Evans et al. ..... 606/185 |
| 5,989,278 | A | | 11/1999 | Mueller |
| 6,030,377 | A | * | 2/2000 | Linhares et al. ..... 606/7 |
| 6,036,677 | A | | 3/2000 | Javier, Jr. et al. |
| 6,045,530 | A | | 4/2000 | Krueger et al. |
| 6,045,565 | A | | 4/2000 | Ellis et al. |
| 6,051,008 | A | | 4/2000 | Saadat et al. |
| 6,056,743 | A | | 5/2000 | Ellis et al. |
| 6,056,760 | A | * | 5/2000 | Koike et al. ..... 606/148 |
| 6,066,126 | A | | 5/2000 | Li et al. |
| 6,093,177 | A | | 7/2000 | Javier, Jr. et al. |
| 6,102,887 | A | | 8/2000 | Altman et al. |
| 6,106,520 | A | | 8/2000 | Laufer et al. |
| 6,126,654 | A | | 10/2000 | Giba et al. |
| 6,165,164 | A | | 12/2000 | Hill et al. |
| 6,179,809 | B1 | | 1/2001 | Khairkhahan et al. |
| 6,197,324 | B1 | * | 3/2001 | Crittenden ..... 424/423 |
| 6,224,584 | B1 | | 5/2001 | March et al. |
| 6,238,389 | B1 | | 5/2001 | Paddock et al. |
| 6,251,104 | B1 | | 6/2001 | Kesten et al. |
| 6,270,496 | B1 | | 8/2001 | Bowe et al. |
| 6,309,370 | B1 | | 10/2001 | Haim et al. |
| 6,322,548 | B1 | | 11/2001 | Payne et al. |
| 6,589,232 | B1 | | 7/2003 | Mueller |
| 6,613,062 | B1 | | 9/2003 | Leckrone et al. |
| 6,620,139 | B1 | | 9/2003 | Plicchi et al. |
| 6,638,233 | B2 | | 10/2003 | Corvi et al. |
| 6,905,476 | B2 | | 6/2005 | Ponzi |
| 7,094,201 | B1 | | 8/2006 | Stokes et al. |
| 2004/0010231 | A1 | | 1/2004 | Leonhardt |

FOREIGN PATENT DOCUMENTS

| | | | |
|---|---|---|---|
| EP | 0853921 | A2 | 7/1998 |
| EP | 0868923 | A2 | 10/1998 |
| EP | 0876796 | A2 | 11/1998 |
| EP | 0895752 | A2 | 2/1999 |
| WO | WO 86/03122 | | 6/1986 |
| WO | WO 86/03122 | A1 | 6/1986 |
| WO | WO 92/10142 | A1 | 6/1992 |
| WO | WO 96/25097 | | 8/1996 |
| WO | WO 96/26675 | | 9/1996 |
| WO | WO 96/35469 | | 11/1996 |
| WO | WO 97/10753 | | 3/1997 |
| WO | WO 97/13471 | | 4/1997 |
| WO | WO 98/05307 | | 2/1998 |
| WO | WO 98/17186 | | 4/1998 |
| WO | WO 98/38916 | | 9/1998 |
| WO | WO 98/39045 | | 9/1998 |

OTHER PUBLICATIONS

PCT Communication—Supplementary European Search Report, Aug. 3, 2001, 3 pages.

PCT International Search Report Mar. 18, 1998, 4 pages.

PCT Notification of Transmittal of International Preliminary Examination Report, Apr. 15, 1999, 13 pages.

PCT Written Opinion, Dec. 23, 1998, 4 pages.

Mandrusov, Membrane-Based Cell Affinity Chromatography to Retrieve Viable Cells, Biotechnol, Prob. 1995, 11, 208-213, Artificial Organs Research Laboratory, Department of Chemical Engineering, Material Sciences and Metallurgy, Columbia University, New York, New York 10027, and Lousville, Lousville, Kentucky 40292.

Assmus, Tranplantation of Progenitor Cells and Regeneration Enhancement in Acute Myocardial Infarction (TOPCARE-AMI), Clinical Investigation and Reports, Oct. 8, 2002, pp. 3009-3017, Department of Molecular Cardiology and Department of Hematology (H.M., D.H.) University of Frankfurt, Frankfurt, Germany, Circulation availabe at http://www.circulationha.org DOI: 10.1161/01.CIR.0000043246.74879CD.

The PMR™ Procedure, http://www.cardiogenesis.com/percutaneous/procedure.html, Jan. 27, 1999.

PMR Poduct, Axcis™ PMR. System, http://www.cardiogenesis.com/percutaneous/product.html, Jan. 27, 1999.

Cooley, Denton A., M.D. et al., "Transmyocardial Laser Revascularization: Clinical Experience with Twelve-Month Follow-Up," The Journal of Thoracic and Cardiovascular Surgery, (Apr. 1996), pp. 791-799.

Cooley, Denton A., M.D. et al., "Transmyocardial Laser Revascularization: Anatomic Evidence of Long-Term Channel Patency," Texas heart Institute Journal, vol. 21, No. 3 (1994), pp. 220-224.

Fenton II, John W. et al., "Thrombin and Antithrombotics," Seminars in Thrombosis and Hemostasis, vol. 24, No. 2, 1998, pp. 87-91.

Folkman, Judah, "Angiogenic Therapy of the Human Heart," Circulation, 1998; 97:628-629.

Frazier, O.H., M.D., et al., "Myocardial Revascularization With Laser: Preliminary Findings," Supplement II Circulation, vol. 92, No. 9, (Nov. 1995), pp. II-58-II-65.

Hardy, Roger Ian, et al., "A Histologic Study of Laser-Induced Transmyocardial Channels," Lasers in Surgery and Medicine, (1987), pp. 6:563-573.

Henry, Timothy D., "Can We really Grow New Blood Vessels," The Lancet, vol. 351, Jun. 20, 1998, pp. 1826-1827.

Hershey, John E. et al., "Transmyocardial Puncture Revascularization: A Possible Emergency Adjunct to Arterial Implant Surgery," Geriatrics, (Mar. 1969), pp. 101-108.

Horvath; Keith A., M.D., et al., "Recovery and Viability of an Acute Myocardial Infarct After Transmyocardial Laser Revascularization," Journal of American College of Cardiology, vol. 25, No. 1 (Jan. 1995), pp. 258-263.

Horvath, Keith A., M.D., et al., "Transmyocardial Laser Revascularization: Operative Techniques and Clinical Results at Two Years," The Journal of Thoracic and Cardiovascular Surgery, (May 1996) pp. 1047-1053.

Khazei, Hassan A., et al., "Myocardial Canalization: A New Method of Myocardial Revasularization," The Annals of Thoracic Surgery, vol. 6, No. 2, (Aug. 1968) pp. 163-171.

Knighton, David R. et al., "Role of Platelets and Fibrin in the Healing Sequence," Annals of Surgery, vol. 196, No. 4, Oct. 1982, pp. 379-388.

Kohmoto, Takushi, M.D., et al., "Does Blood Flow Through Holmium: YAG Transmyocardial Laser Channels?," Ann. Thorac. Surg., (1996) pp. 61: 861-868.

Kuzela, Ladislaw, et al., "Experimental Evaluation of Direct Transventricular Revascularization," Journal ofThoracic and Cardiovasuclar Surger, vol. 57, No. 6, (Jun. 1969), pp. 770-773.

Lee, Garrett, M.D., "Effects of Laser Irradiation Delivered by Flexible Fiberoptic System on the Left Ventricular Internal Myocardium," American Heart Journal, (Sep. 1983), pp. 587-590.

Losordo, Douglas W. et al., "Gene Therapy for Myocardial Angiogenesis Initial Clinical Results With Direct Myocardial Injection of phVEGF.sub.165 as Sole Therapy for Myocardial Ischemia," Circulation, 1998; 98: 2800-2804.

Maloney, James P. et al., "In Vitro Release of Vascular Endothelial Growth Factor During Platelet Aggregation," American Physiological Society, H1054-H1061, 1998.

Miyazono, Kohei et al., "Platelet-Derived Endothelial Cell Growth Factor," Progress in Growth Factor Research, vol. 3, 1991, pp. 207-217.

Pipili-Synetos, E. et al., "Evidence That Platelets Promote Tube Formation By Endothelial Cells on Matrigel," British Journal of Pharmacology, vol. 125, 1998, pp. 1252-1257.

Simons, Michael et al., "Food for Starving Hearts," Nature Medicine, vol. 2, No. 5, May 1996, pp. 519-520.
Sen, P.K. et al., "Further Studies in Multiple Transmyocardial Acupuncture as a Method of Myocardial Revascularization," Surgery, vol. 64, No. 5, (Nov. 1968), pp. 861-870.
Tsopanoglou, Nikos E. et al., "Thrombin Promotes Angiogenesis By a Mechanism Independent of Fibrin Formation," American Physiological Society, 0363-6143/93, C1302-1307.
Thaning, Otto, "Transmyocardial Laser Revascularisation in South Africa," SAMJ, vol. 85, No. 8 (Aug. 1995) pp. 787-788.
Verheul, Henk M.W. et al., "Platelet: Transporter of Vascular Endothelial Growth Factor," Clinical Cancer Research, vol. 3, Dec. 1997, pp. 2187-2190.
Von Oppell, Ulrich O., "Transmyocardial Laser Revascularisation," SAMJ, vol. 85, No. 9, (Sep. 1995), p. 930.
Wakabayashi, Akio, "Myocardial Boring For the Ischemic Heart," Arch. Surgery, vol. 95, (Nov. 1967), pp. 743-752.
Wartiovaara, Ulla et al., "Peripheral Blood Platelets Express VEGF-C and VEGF Which Are Released During Platelet Activation," Thromb Haemost, 1998, 80:171-5.
Washington Adventist Hospital, "Washington Area Cardiologist Performs First State-of-the-Art Heart Procedure In U.S.," PR Newswire, Dec. 15, 1999, 2 pages.
White, Manuel et al., "Multiple Transmyocardial Puncture Revascularization in Refractory Ventricular Fibrillation due to Myocardial Ischemia," The Annals of Thoracic Surgery, vol. 6, No. 6, (Dec. 1968), pp. 557-563.
A Collection of Abstracts, Society of Thoracic Surgeons, 1999.

* cited by examiner

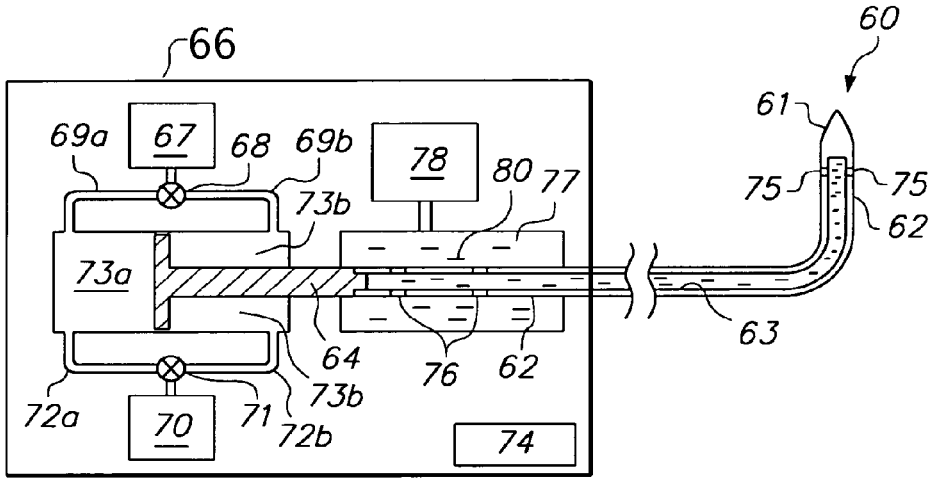
FIG. 5
Amended

APPARATUS AND METHODS FOR STIMULATING REVASCULARIZATION AND/OR TISSUE GROWTH

Matter enclosed in heavy brackets [ ] appears in the original patent but forms no part of this reissue specification; matter printed in italics indicates the additions made by reissue.

REFERENCE TO RELATED APPLICATIONS

[The present application is a continuation-in-part application of commonly assigned U.S. patent application Ser. No. 08/863,791, now U.S. Pat. No. 5,931,848, Ser. No. 08/863,877, now U.S. Pat. No. 5,910,150, and Ser. No. 08/863,925, now U.S. Pat. No. 5,941,839, all filed May 27, 1997.] *The present application is a continuation-in-part application of commonly assigned U.S. patent application Ser. No. 08/863,791, now U.S. Pat. No. 5,931,848, and Ser. No. 08/863,877, now U.S. Pat. No. 5,910,150, and Ser. No. 08/863,925, now U.S. Pat. No. 5,941,893, all filed May 27, 1997, all of which claim the benefit of the filing date of U.S. provisional patent application Ser. No. 60/032,196, filed Dec. 2, 1996.*

FIELD OF THE INVENTION

The present invention relates to apparatus and methods for stimulating revascularization and tissue growth in an interior region of an organ or vessel, such as the heart. More particularly, the present invention provides a device that enables a clinician to stimulate a healing response, or deposit a bioactive agent at, a series of sites within in interior region of an organ or vessel to stimulate revascularization.

BACKGROUND OF THE INVENTION

A leading cause of death in the United States today is coronary artery disease, in which atherosclerotic plaque causes blockages in the coronary arteries, resulting in ischemia of the heart (i.e., inadequate blood flow to the myocardium). The disease manifests itself as chest pain or angina. In 1996, approximately 7 million people suffered from angina in the United States.

Coronary artery bypass grafting (CABG), in which the patient's chest is surgically opened and an obstructed artery replaced with a native artery harvested elsewhere, has been the conventional treatment for coronary artery disease for the last thirty years. Such surgery creates significant trauma to the patient, requires long recuperation times, and causes a great deal of morbidity and mortality. In addition, experience has shown that the graft becomes obstructed with time, requiring further surgery.

More recently, catheter-based therapies such as percutaneous transluminal coronary angioplasty (PTCA) and atherectomy have been developed. In PTCA, a mechanical dilatation device is disposed across an obstruction in the patient's artery and then dilated to compress the plaque lining the artery to restore patency to the vessel. Atherectomy involves using an end effector, such as a mechanical cutting device (or laser) to cut (or ablate) a passage through the blockage. Such methods have drawbacks, however, ranging from re-blockage of dilated vessels with angioplasty to catastrophic rupture or dissection of the vessel during atherectomy. Moreover, these methods may only be used for that fraction of the patient population where the blockages are few and are easily accessible. Neither technique is suitable for the treatment of diffuse atherosclerosis.

A more recent technique which holds promise for treating a larger percentage of the patient population, including those patients suffering from diffuse atherosclerosis, is referred to as transmyocardial revascularization (TMR). In this method, a series of channels are formed in the left ventricular wall of the heart. Typically, between 15 and 30 channels about 1 mm in diameter and up to 3.0 cm deep are formed with a laser in the wall of the left ventricle to perfuse the heart muscle with blood coming directly from the inside of the left ventricle, rather than traveling through the coronary arteries. Some researchers believe that the resulting channels improve perfusion of the myocardium with oxygenated blood. Apparatus and methods have been proposed to create such channels both percutaneously and intraoperatively (i e., with the chest opened).

U.S. Pat. No. 5,389,096 to Aita et al. describes a catheter-based laser apparatus for use in percutaneously forming channels extending from the endocardium into the myocardium. The catheter includes a plurality of control lines for directing the tip of the catheter. As the laser ablates the tissue during the channel forming process, the surrounding tissue necroses, resulting in fibroid scar tissue surrounding the channels. U.S. Pat. No. 5,380,316 to Aita et al. describes an intraoperative laser-based system for performing TMR.

U.S. Pat. No. 5,591,159 to Taheri describes mechanical apparatus for performing TMR comprising a catheter having an end effector formed from a plurality of spring-loaded needles. The catheter first is positioned percutaneously Within the left ventricle. A plunger is then released so that the needles are thrust into the endocardium. The needles core out small channels that extend into the myocardium as they are withdrawn. The patent suggests that the needles may he withdrawn and advanced repetitively at different locations under fluoroscopic guidance. The patent does not appear to address how tissue is ejected from the needles between the tissue-cutting steps Although it is generally agreed that TMR benefits many patients, researchers do not agree upon the precise mechanism by which TMR provides therapeutic benefits. One theory proposes that TMR channels remain patent for long periods of time, and provide a path by which oxygenated blood perfuses the myocardium. However, relatively recent histological studies indicate that TMR channels may close within a short time following the procedure. For example, Fleischer et al., in "One-Month Histologic Response Of Transmyocardial Laser Channels With Molecular Intervention," Ann. Soc. Thoracic Surg., 62:1051-58 (1996), evaluated histologic changes associated with laser TMR in a 1-month nonischemic porcine model, and was unable to demonstrate channel patency 28 days after TMR.

Other researchers have observed that in laser-based TMR patients, there appears to he enhanced vascularization of the tissue on the margins of the scar tissue resulting from the laser channel-forming process. It has therefore been hypothesized that the act of causing trauma to portions of the myocardium may invoke a regenerative process, that enhances the development of neovascularization and endothelialization in the tissue.

To investigate these alternative theories, researchers have studied the use of gene therapy in promoting blood vessel growth in the tissue surrounding laser TMR channels. In one study, researchers intraoperatively administered a single dose of vascular endothelial growth factor (VEGF) at the time of laser TMR. Although the study showed no significant increase in myocardial vascularity, the researchers hypothesized that a longer duration of VEGF residence may be necessary to stimulate angiogenesis.

In view of the foregoing, it would be desirable to provide apparatus and methods for stimulating revascularization and tissue growth in an interior region of an organ or vessel, such as the heart, by stimulating native revascularization and tissue growth mechanisms.

It would also be desirable to provide apparatus and methods for stimulating revascularization and tissue growth by controlling the placement and size of tissue treatment sites, thereby resulting in a controlled degree of scar tissue formation.

It would be still further desirable to provide apparatus and methods for stimulating revascularization and tissue growth by depositing a controlled amount of a bioactive agent, such as an angiogenic growth factor, at the treatment sites.

SUMMARY OF THE INVENTION

In view of the foregoing, it is an object of this invention to provide apparatus and methods for stimulating revascularization and tissue growth in an interior region of an organ or vessel, such as the heart, by stimulating native revascularization and tissue growth mechanisms.

It is another object of the present invention to provide apparatus and methods for stimulating revascularization and tissue growth by controlling the placement and size of tissue treatment sites, thereby resulting in a controlled degree of scar tissue formation.

It is a still further object of this invention to provide apparatus and methods for stimulating revascularization and tissue growth by depositing a controlled amount of a bioactive agent, such as a drug or an angiogenic growth factor, at the treatment sites.

These and other objects of the present invention are accomplished by providing apparatus having a directable end region carrying an end effector that induces trauma at a treatment site to stimulate revascularization. The apparatus may optionally include electrodes for depositing RF energy to form a controlled degree of scar tissue formation, means for depositing a controlled amount of a bioactive agent at the treatment site, or both.

Apparatus constructed in accordance with the present invention comprises a catheter having a longitudinal axis, an end region that is deflectable relative to the longitudinal axis, and a tissue piercing end effector. The end effector may optionally include an RF electrode for causing a controlled degree of necrosis at a treatment site, the capability to deposit a controlled amount of a bioactive agent at the treatment site, or both.

Methods of using the apparatus of the present invention to stimulate revascularization and/or tissue growth are also provided.

BRIEF DESCRIPTION OF THE DRAWINGS

Further features of the invention, its nature and various advantages will be more apparent from the accompanying drawings and the following detailed description of the preferred embodiments, in which:

FIG. 5 is a schematic view of an alternative illustrative arrangement for driving an end effector adapted to deliver a bioactive agent.

DETAILED DESCRIPTION OF THE INVENTION

The present invention relates generally to apparatus and methods for treating a plurality of tissue sites within a vessel or organ to stimulate tissue growth and revascularization. The apparatus of the present invention comprises a catheter having an end region that may be selectively articulated to a position at an angle relative to the longitudinal axis of the catheter, including a position substantially orthogonal to the longitudinal axis.

The end region carries a tissue piercing end effector to induce trauma to stimulate native tissue repair and revascularization mechanisms. The end effector may optionally include an RF electrode to cause a controlled degree of necrosis, means for depositing a controlled amount of a bioactive agent at the treatment site, or both. The deflectable end region of the catheter provides precise control over the location of the end region, and thus, the end effector.

Figure 1:
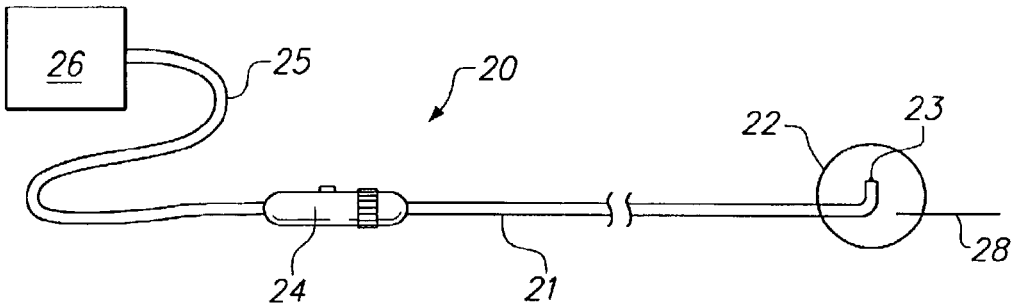
FIG. 1 is a view of an illustrative embodiment of apparatus constructed in accordance with the present invention.

Referring to FIG. 1, illustrative apparatus 20 constructed in accordance with the present invention is described. Apparatus 20 comprises catheter 21 having deflectable end region 22, end effector 23 and handle 24, cable 25 and controller 26. Apparatus 20 is coupled via cable 25 to controller 26. End effector 23, described in greater detail hereinbelow, pierces myocardial tissue, with or without coring, to attain a treatment goal.

Figure 2:
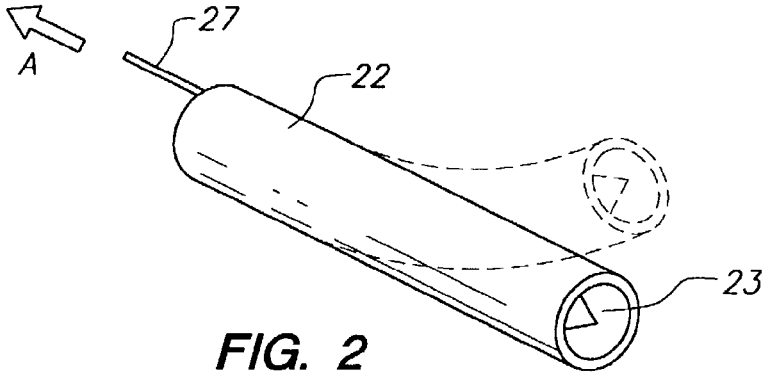
FIG. 2 is a perspective view of an end region and end effector of the apparatus of FIG. 1.

End region 22 includes one or more control wires 27 disposed for sliding movement within catheter 21, such as described in U.S. Pat. Nos. 5,389,073 and 5,330,466 to Imran, which are incorporated herein by reference. Application of a predetermined proximal force on control wire 27 (indicated by arrow A), deflects end region 23 a predetermined amount (shown in dotted lines in FIG. 2). Accordingly, end region 23 may be moved between a transit position, parallel to longitudinal axis 28 of catheter 21 and a working position (as shown) substantially orthogonal to longitudinal axis 28.

In a preferred embodiment, wherein the end effector comprises a flexible wire having a sharpened tip, controller 26 includes a hydraulic or pneumatic piston, valve assembly and control logic for extending and retracting the end effector beyond the distal endface of end region 23 responsive to commands input at handle assembly 24 or a footpedal (not shown) Controller 26 optionally may further contain RF generator circuitry for energizing electrodes disposed on the end effector to cause a controlled degree of necrosis at the treatment site. Alternatively, or in addition, controller 26 may include a source of a bioactive agent, and means for delivering controlled amounts of the bioactive agent to the treatment site.

Figure 3:
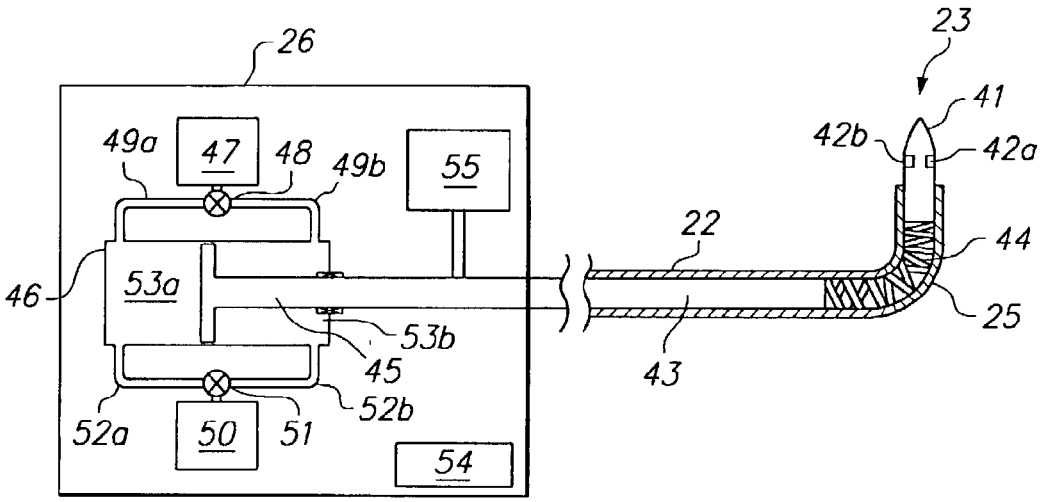
FIG. 3 is schematic view of an illustrative arrangement for driving the end effector of FIG. 1.
Figure 4:
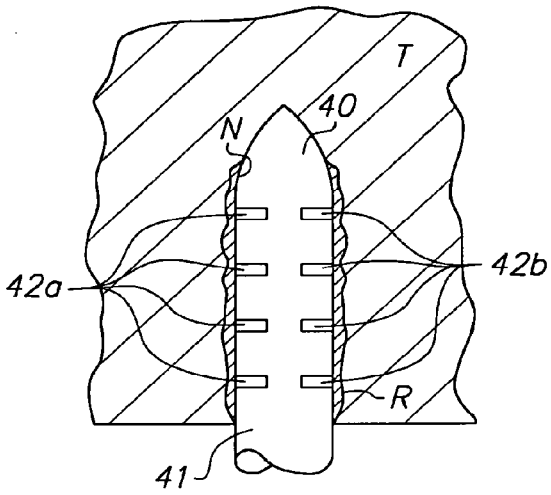
FIG. 4 is a partial side view of the end effector of the apparatus of FIG. 1.

Referring now to FIG. 3, end effector 23 and controller 26 of a first embodiment are described. In FIG. 4, most of catheter 21 and handle 24 have been omitted for clarity. End effector 23 comprises tissue piercing cone 41 having optional first and second RF electrodes 42a and 42b, respectively. End effector preferably comprises a rigid material that retains a sharp tip, such as stainless steel Drive shaft 43, which extends through cable 25 of FIG. 1, is coupled to end effector 23 via flexible coupling 44 at its distal end, and to piston 45 at its proximal end. Drive shaft 43 is disposed for reciprocation in end region 22 responsive to movement of piston 45. Drive shaft 43 may comprise a single or braided plastic or metal alloy wire, while flexible coupling 44 comprises a sturdy but flexible plastic or metal alloy.

Piston 45 is enclosed within cylinder 46 for proximal and distal movement. High pressure source 47 is connected to valve 48 and pressure lines 49a and 49b; low pressure source 50 is connected to valve 51 and pressure lines 52a and 52b. Pressure lines 49a and 52a communicate with proximal volume 53a of cylinder 46, whereas pressure lines 49b and 52b communicate with distal volume 53b of cylinder 46. Valves 48 and 51 are synchronized so that when high pressure source 47 is coupled to pressure line 49a (but not 49b), low pressure source 50 is coupled to line 52b (but not 52a), thus driving piston 45 in the distal direction.

Likewise, when valve 48 couples high pressure source 47 to pressure line 49b (but not 49a), and valve 51 couples low pressure source 50 to line 52a (but not 52b), piston 45 is driven in the proximal direction. Valves 48 and 51 are coupled by wiring (not shown) to control logic 54, which actuates the valves responsive to control commands received from handle assembly 26 or a footpedal (not shown). Cylinder 46 may employ any suitable medium for moving piston 45, and may be either pneumatic or hydraulic.

Controller 26 optionally includes RF generator circuitry 55 which generates a high frequency (e.g., greater than 100 MHZ) voltage signal. RF generator circuitry 55 is coupled via suitable bushings and conductors (not shown) to electrodes 42a and 42b. Electrodes 42a and 42b may be arranged to conduct current through tissue located in contact them, in a bipolar mode, or may conduct current through the tissue and to a ground plate (not shown) in a monopolar mode. In embodiments of controller 26 where RF generator circuitry 55 is provided, control logic 54 may be programmed to energize electrodes 42a and 42b when piston 45 has attained its maximum distal stroke. Control logic 54 may energize electrodes 42a and 42b for a user selected interval to provide a controlled degree of necrosis in the tissue surrounding the treatment site created by end effector 23.

Referring now also to FIG. [6] *3*, when piston 45 is driven in the distal direction, end effector 23 extends beyond the distal endface of catheter 21 and pierces and extends into tissue T. End effector 23 thereby induces trauma to tissue T in the form of needle track N. If electrodes 42a and 42b and RF generator circuitry 55 are provided, control logic 55 may energize the electrodes to cause necrosis of tissue T in a region R surrounding the end effector. Control logic 54 then reverses the orientation of valves 48 and 51, thus causing end effector 23 to be retracted from tissue T and into end region 22.

Applicants expect that the trauma caused by needle track N will stimulate naturally occurring mechanisms to repair the wound at the treatment site. It is further expected that by generating a matrix of treatment sites, a network of small vessels may become established in the tissue as it heals. In addition, by providing a controlled degree of necrosis, a preselected degree of scar tissue may be induced, thus mimicking the conditions observed to induce revascularization at the margins of laser-formed TMR channels.

Figure 6:
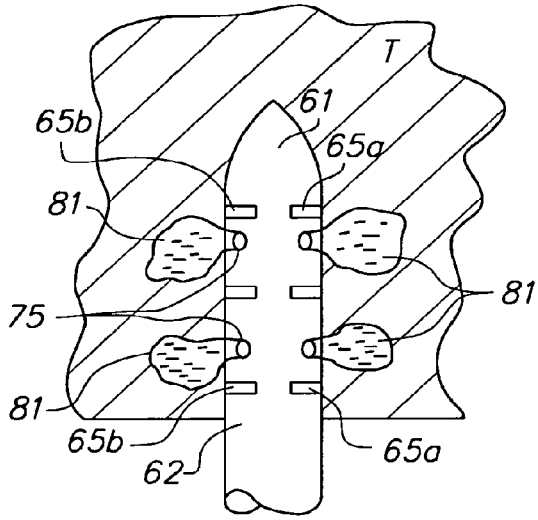
FIG. 6 is a partial side view of the end effector of the apparatus of FIG. 5.

With respect to FIGS. 5 and 6, an alternative embodiment of the end effector and controller of the present invention is described. Once again, catheter 21 (except for end region 22) and handle 24 have been omitted from FIG. 5 for clarity End effector 60 comprises non-coring tissue piercing cone 61 affixed to drive shaft 62. Drive shaft 62 includes lumen 63, and extends through cable 25 of FIG. 1 Drive shaft 62 is coupled to piston 64 at its proximal end, and is disposed for reciprocation in the guide tube (not shown) responsive to movement of piston 64. Drive shaft 62 preferably comprises a thin-walled but flexible plastic or metal alloy tube. End effector 60 may optionally include electrodes 65a and 65b for applying an RF voltage potential to the tissue to cause a controlled degree of necrosis, as described hereinabove with respect to the embodiment of FIGS. 3 and 4.

Piston 64 is enclosed within a cylinder in controller 66 for proximal and distal movement. High pressure source 67 is connected to valve 68 and pressure lines 69a and 69b; low pressure source 70 is connected to valve 71 and pressure lines 72a and 72b. Pressure lines 69a and 72a communicate with proximal volume 73a of the cylinder, whereas pressure lines 69b and 72b communicate with distal volume 73b of the cylinder Valves 68 and 71 are synchronized as described hereinabove with respect to like components of FIG. 4, so as to extend and retract end effector 60 under the control of control logic 74 responsive to control commands received from handle assembly 26.

Drive shaft 62 includes a plurality of outlet ports 75 located adjacent to cone 61 and a plurality of inlet ports 76 disposed in chamber 77. Chamber 77 contains bioactive agent 80 suspended in a biocompatible high viscosity liquid or paste, and is selectively pressurized by pressure source 78. Bioactive agent 80, may comprise a drug or an angiogenic growth factor, for example, vascular endothelial growth factor (VEGF), fibroblast growth factor, type I (FGF-I) or type II (FGF-II), a gene vector, cardio myocytes, or other suitable agent for stimulating tissue growth and/or revascularization.

Inlet ports 76 and outlet ports 75 communicate with lumen 63. In accordance with one aspect of the present invention, when high pressure source 78 is actuated to pressurize chamber 77, a controlled amount of bioactive agent 80 is injected into inlet ports 76 of lumen 63. This in turn causes an equal amount of bioactive agent 80 to be expelled through outlet ports 75 of end effector 60 into the adjacent tissue. Control logic 74 preferably is programmed to actuate high pressure source 78 when piston 64 has attained its maximum distal stroke. Controller 66 may in addition include an RF generator circuitry similar to RF generator circuitry 55 of the embodiment of FIG. 3 for energizing electrodes 65a and 65b.

With respect to FIG. 6, when piston 64 is driven in the distal direction, end effector 60 extends beyond the distal endface of the catheter and pierces and extends into tissue T. End effector 60 thereby causes trauma to tissue T in the form of needle track N. Once end effector 60 reaches its maximum depth, control logic 74 actuates high pressure source 78, causing a controlled amount of bioactive agent 80 to be expelled through outlet ports 75 into the tissue.

If the bioactive agent exits the ports with sufficiently high velocity, it is expected that the bioactive agent will form pockets 81 in the tissue. Alternatively, if the bioactive agent exits outlet ports 75 at lower velocity, it is expected that the bioactive agent will form a layer that coats the interior surface of needle track N. Once the bioactive agent has been deposited, control logic 74 reverses the orientation of valves 68 and 71, thus causing end effector 60 to be retracted from tissue T and into the end region of the catheter. If provided, RF electrodes 65a and 65b may be activated to cauterize tissue in the vicinity of needle track N.

As described hereinabove, applicants expect that the trauma caused by needle track N will stimulate the release of naturally tissue regenerative mechanisms to repair the wound at the treatment site. Moreover, the introduction of bioactive agent 80 along needle track N is expected to further stimulate revascularization By generating a matrix of treatment sites within which a bioactive agent has been deposited, it may be possible to promote the development of a network of small vessels that will perfuse the tissue.

Figure 7A:
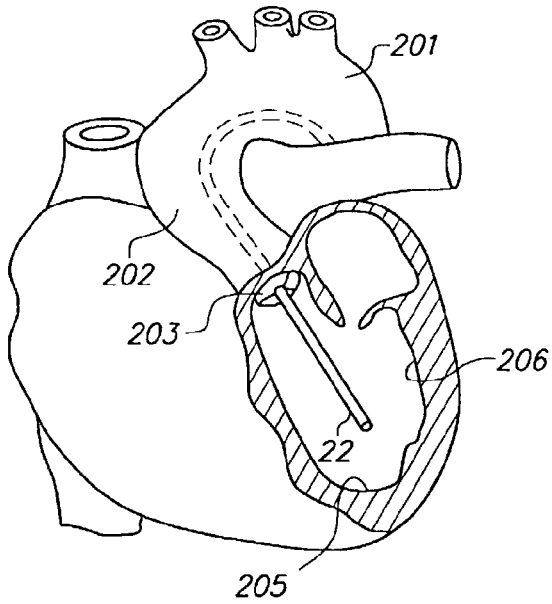
FIGS. 7A to 7C are views illustrating operation of the apparatus of FIG. 1.
Figure 7B:
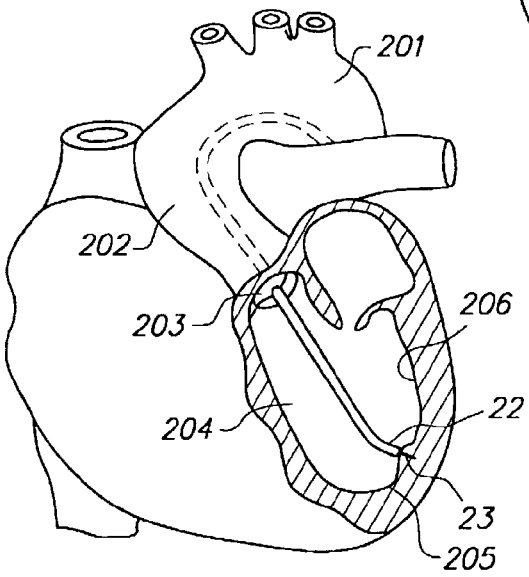
Figure 7C:
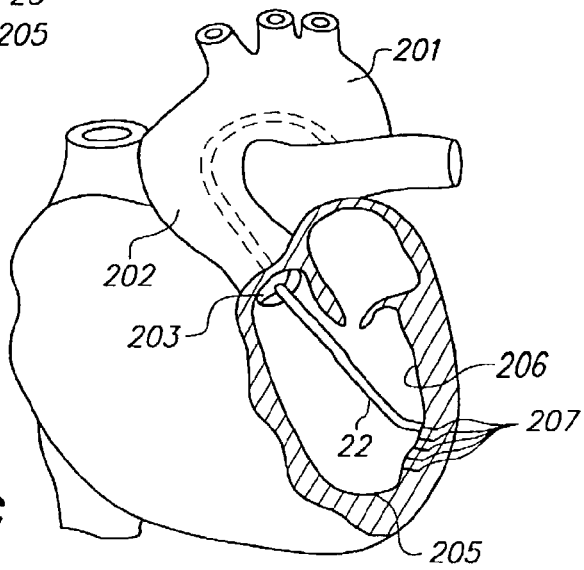

Referring now to FIGS. 7A–7C, operation of apparatus 20 in the context of treating a series of treatment sites to stimulate revascularization in left ventricular myocardium is described. In FIG. 7A, end region 22 of apparatus 20 is shown positioned in a patient's left ventricular cavity, using techniques which are per se known. Specifically, end region 22 of apparatus 20 is inserted via a femoral artery, and is maneuvered under fluoroscopic guidance in a retrograde manner up through the descending aorta, through aortic arch 201, and down through ascending aorta 202 and aortic valve 203 into left ventricle 204. As will of course be understood, insertion of apparatus 20 into the left ventricle is with end region 22 in its transit position.

Previously known imaging techniques, such as ultrasound, MRI scan, CT scan, or fluoroscopy, may be used to verify the location of the end region 22 within the heart. Alternatively, means may be provided in end region 22 for emitting an ultrasonic signal which is detectable using an ultrasound imaging system outside of the patient. For example, a piezoelectric transducer may be affixed to the tip of the catheter and tuned to a frequency of a color Doppler ultrasound imaging system so as to appear as a bright orange or yellow spot on the display of the ultrasound system. Yet another way to detect the location of end region 22 is by pinpointing the delay time of an EKG signal at the point of detection, using an electrode disposed in end region 22. By looking at the morphology as well as the temporal characteristics of the EKG signal, the vertical position of the catheter within the heart chamber may be determined.

Referring to FIG. 7B, once end region is located adjacent a desired portion of the endocardial surface, end region 22 is deflected to its working position, for example, by operating control wire 27. In this manner end effector 23 is disposed against a surface of the endocardium to be treated.

Controller 26 is then actuated to cause end effector 23 to pierce and extend into the interior of left ventricular wall 206. When the end effector reaches its maximum depth, a burst of RF energy may be applied, if desired, to necrose a depth of tissue, an amount of a bioactive agent may be deposited at the treatment site, or both. Controller 26 then withdraws end effector 23 from the tissue.

As shown in FIG. 7C, a series of vertically aligned spaced-apart needle tracks 207 may he formed in left ventricular wall 206 by repositioning end region 22 using control wire 27. End effector 23 is then advanced to form a further needle track 207 in the tissue.

The foregoing methods enable a matrix of channels to be formed illustratively in the left ventricular wall. It will of course be understood that the same steps may be performed in mirror image to produce a series of needle tracks in the septal region. It is believed that the needle tracks may have a beneficial effect if formed anywhere on the walls of the heart chamber, including the septum, apex and left ventricular wall; the above-described apparatus provides this capability In addition, a stabilization assembly may be employed, for example, as described in copending, commonly assigned U.S. patent application Ser. No. 08/863,877, filed May 27, 1997, to counteract any reaction forces generated by operation of end effector 23.

Figure 8:
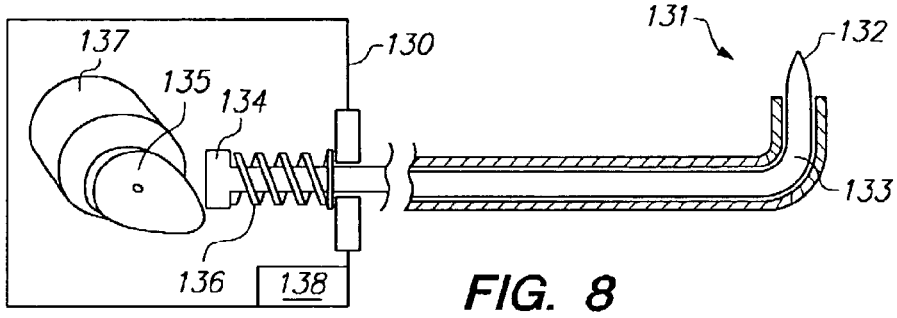
FIG. 8 is a schematic view of another alternative arrangement for driving the end effector of the apparatus of FIG. 1.

In FIG. 8, an alternative arrangement for driving the end effector of the present invention is described. In controller 130 of FIG. 8, the piston and cylinder of controller 26 of FIG. 1 are replaced with a mechanical drive system. As in FIGS. 3 and 4, most of the catheter and handle have been omitted for clarity. End effector 131 comprises non-coring sharpened tip 132 coupled to drive shaft 133. Drive shaft 133 is coupled at its proximal end to push rod 134. Push rod 134 is biased against eccentric cam 135 by spring 136. Cam 135 is mounted on motor 137, which rotates cam 135 through one revolution responsive to commands from control logic 138. Control logic 138, in turn, actuates motor 137 responsive to commands received, for example, by a button on handle 24 (see FIG. 1). Thus, controller 130 extends and retracts end effector 131 to create a needle track in the tissue.

As will of course be apparent to one of skill in designing catheter-based systems, controller 130 may optionally include either the RF generator circuitry and electrodes of the embodiment of FIG. 3, the bioactive agent delivery system described with respect to the embodiment of FIG. 5, or both. As will be further apparent, the specific drive arrangements described hereinabove are intended to be illustrative, and other mechanisms may be readily employed. For example, the specific configuration of the pressure sources, pressure lines and the valves in FIGS. 3 and 5 are intended to be merely illustrative. Equivalent mechanisms for extending and retracting the end effector may be readily employed within the scope of the present invention. Thus, for example, the end effector may be spring loaded so as to be biased in the extended position and reset after having been extended to form each needle track.

Figure 9:
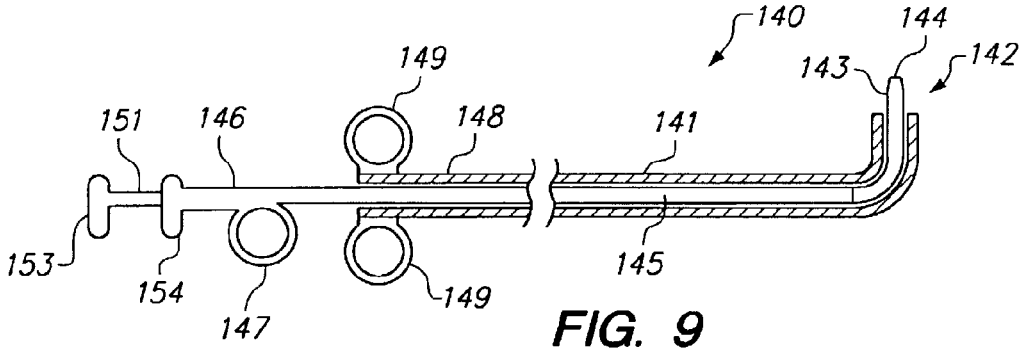
FIG. 9 is a schematic view of a yet another further alternative arrangement for driving an end effector constructed in accordance with the present invention.
Figure 10A:
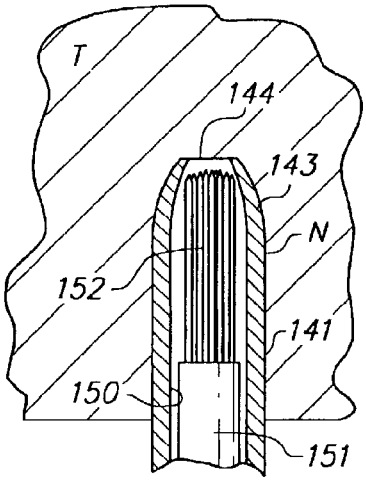
FIGS. 10A and 10B are, respectively, partial side sectional views illustrating operation of another end effector of the present invention.
Figure 10B:
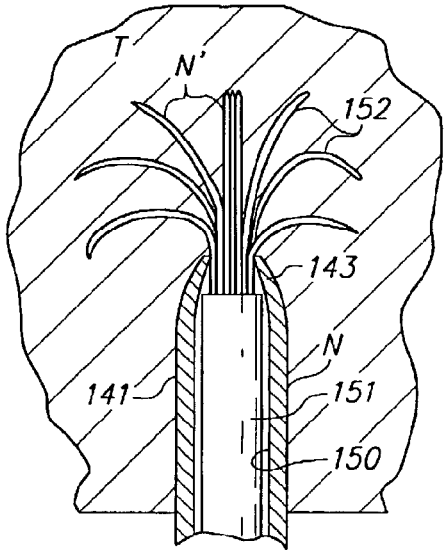

Referring now to FIGS. 9, 10A and 10B, a further alternative embodiment of a drive system and end effector suitable for use in the present invention are described. In apparatus 140 of FIG. 9, it is again to be understood that the handle and most of the catheter have been omitted for clarity In apparatus 140, a manual drive arrangement has been substituted for the controller of the previously described embodiments. In particular, end effector 142 comprises tip 143 having aperture 144 coupled to the distal end of drive shaft 145. Proximal end 146 of drive shaft 145 includes actuator ring 147, and proximal end 148 of catheter 141 includes rings 149. As will be apparent, drive shaft 144 may be driven in the distal direction to extend end effector 142 by squeezing actuator ring 147 towards rings 149.

With respect to FIG. 10A, drive shaft 145 includes lumen 150 and push wire 151 disposed within lumen 150. Push wire 151 terminates at its proximal end in a plurality of fine wires 152. Wires 152 may comprise, for example, nickel-titanium, and are constructed so that when they extend through aperture 144, the wires diverge (see FIG. 10B). Push wire 151 extends through lumen 150 of drive shaft 145 and terminates in button 153. By gripping flange 154 provided on proximal end 146 of drive shaft 145, button 153 may be depressed toward flange 154, thereby extending wires 152 through aperture 144.

Figure 11A:
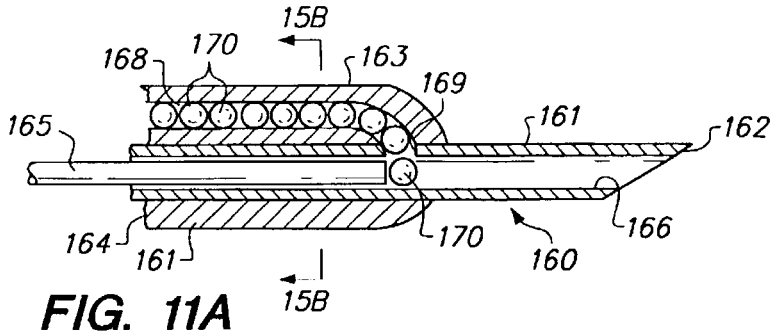
FIGS. 11A and 11B are, respectively, a partial side sectional view and cross-sectional view of a further alternative embodiment of an end effector of the present invention.
Figure 11B:
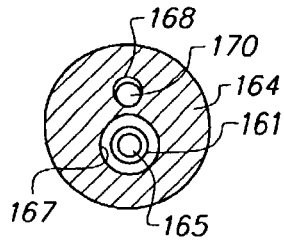

FIG. 10A shows end effector 142 extended to pierce and extend into tissue T to form needle track N, for example, by squeezing actuator ring 147 towards ring 149. As will of course be understood, this step occurs after the catheter has been disposed within an organ or vessel as described above with respect to FIGS. 7A and 7B. FIG. 10B illustrates that extension and retraction of wires 152 generates a matrix of additional needle tracks N' Applicant expects that, like the application of RF energy to form a controlled layer of scar tissue, or the deposition of an amount of a bioactive agent, the matrix of needle tracks N' will further stimulate revascularization in the tissue With respect to FIGS. 11A and 11B, an alternative embodiment of an end effector is described for depositing a bioactive agent in a pelletized form. In FIGS. 11, it is to be understood that the handle assembly and most of the catheter have been omitted. End effector 160 comprises tube 161 including beveled non-coring tip 162 mounted in distal end 163 of catheter 164. Push rod 165 is disposed for reciprocation in lumen 166 of tube 161. As shown in FIG. 11B, catheter 164 includes lumen 167 in which tube 161 is disposed, and lumen 168 through which bioactive pellets 170, illustratively, spherical beads, are advanced to end effector 160. Lumen 168 includes passageway 169 through which a pellet passes to engage push rod 165 for delivery.

In accordance with one aspect of the present invention, pellets 170 comprise a bioactive agent, as described hereinabove, disposed in a biodegradable binder, such as polycaprolactone or polylactic acid. Pellets 170 are sized to advance through lumen 168 freely and without bunching, so that when posh rod is retracted in the proximal direction past the proximal edge of passageway 169, a single pellet 170 passes into lumen 166 of tube 161. While pellets 170 are illustrative spherical, it is to be understood that the bioactive agent may be readily formed into any of a number of other shapes, such as rods, cones, granules, etc., and that the above-described delivery system may be readily adapted to such other pelletized forms.

Referring now to FIGS. 12A to 12D, operation of the apparatus of FIGS. 11 is described. Apparatus including end effector 160 first is disposed within an internal organ, such as the left ventricle, as described hereinabove with respect to FIGS. 7A to 7C. End effector 160 then is oriented so as to be positioned at a desired angle, e.g. perpendicular, to tissue T to be treated. While end effector 160 is being maneuvered into position, posh rod 165 is extended so that distal endface 171 extends past the distal edge of passageway 169, thereby confining pellets 170 within lumen 168. End effector 160 is urged in the distal direction to form needle track N, and so that tip 162 penetrates tissue T until catheter 164 abuts against the endocardium (shown in FIG. 12A).

Figure 12A:
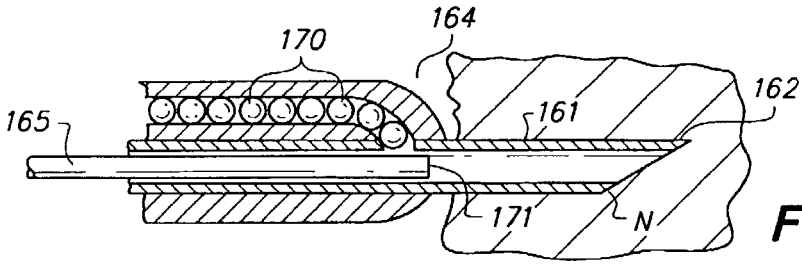
FIGS. 12A to 12D are views illustrating operation of the end effector of FIGS. 11 to deposit a pellet of a bioactive agent at a treatment site.
Figure 12B:
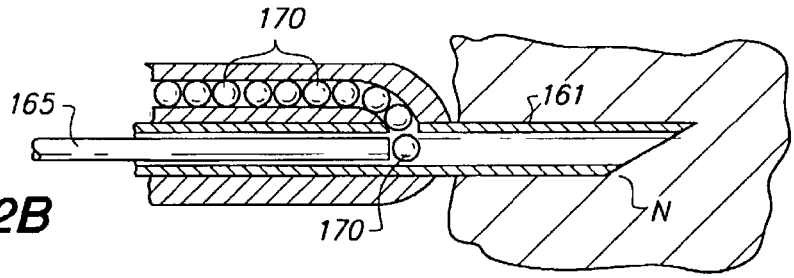

Push rod 165 then is retracted in the proximal direction, so that distal endface 171 is positioned proximally of the proximal edge of passageway 169. This in turn permits a single pellet 170 to advance through passageway 169 into lumen 166, as shown in FIG. 12B. Because pellets 170 are preferably only slightly smaller than the diameter of lumen 166, when a single pellet 170 has advanced into lumen 166, it will block other pellets from passing through passageway 169 into lumen 166. Alternatively, pellets 170 may be sized so that a predetermined number of pellets pass into lumen 166 each time push rod 165 is retracted proximally.

Figure 12C:
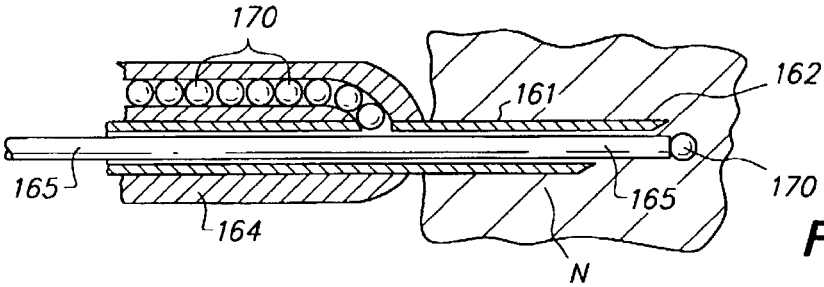
Figure 12D:
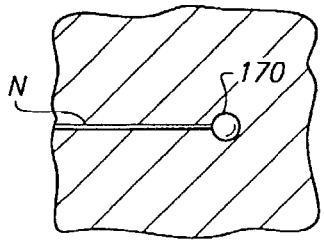

Push rod 165 then is driven in the distal direction, urging pellet 170 to the end of needle track N, as illustrated in FIG. 12C If RF electrodes are provided on tip 162, such electrodes may be energized to necrose a predetermined thickness of tissue in the vicinity of tip 162. End effector 160 then is withdrawn, leaving pellet 170 within needle track N in tissue T. As described hereinabove, pellet 170 preferably comprises a biodegradable substance that elutes a suitable bioactive agent into the tissue surrounding the pellet over a preselected period of time. It is expected that by depositing a bioactive substance within tissue T, tissue revascularization and growth may be stimulated, as described hereinabove. End effector 160 then is moved to another location and the foregoing process repeated to seed a plurality of pellets 170.

While preferred illustrative embodiments of the invention are described above, it will he apparent to one skilled in the art that various changes and modifications may be made therein without departing from the invention, and the appended claims are intended to cover all such changes and modifications that fall within the true spirit and scope of the invention.

What is claimed is:

1. Apparatus for treating an interior region of a cardiac chamber, the apparatus comprising:

a catheter configured for insertion into a cardiac chamber, the catheter having a deflectable end region;

an end effector disposed [within] *distal to* the delectable end region, the end effector adapted to form a needle track at a treatment site in an interior region of the cardiac chamber, the end effector movable between a first position, wherein the end effector is retracted within the end region, and a second position, wherein the end effector is extended beyond a distal endface of the catheter; and means for moving the end region between the first and second positions, wherein the end effector further comprises means for depositing a controlled amount of a bioactive agent at the treatment site *and wherein the catheter has a plurality of lumens, one of which contains the bioactive agent and wherein the catheter has a conductor extending from a proximal end of the catheter to an electrode which is distal to the deflectable end region*.

2. The apparatus of claim 1 wherein the end effector comprises a non-coring sharpened tip.

3. The apparatus of claim 1 wherein the end effector further comprises an electrode adapted to deliver RF energy to the treatment site.

4. The apparatus of claim 1 wherein the end effector further comprises a plurality of fine wires, the fine wires movable between a retracted position and an extended position, the plurality of fine wires forming a matrix of additional needle tracks at the treatment site when extended.

5. The apparatus of claim 1 wherein the end effector is coupled to a drive shaft, the apparatus further comprising a controller including a hydraulic mechanism coupled to the drive shaft to extend and retract the end effector.

6. The apparatus as defined in claim 1 wherein the end effector is coupled to a drive shaft, the apparatus further comprising a controller including a pneumatic mechanism coupled to the drive shaft to extend and retract the end effector.

7. The apparatus as defined in claim 1 wherein the end effector is coupled to a drive shaft, the apparatus further comprising a manually actuated mechanism coupled to the drive shaft to extend and retract the end effector.

8. Apparatus for treating an interior region of a cardiac chamber, the apparatus comprising:

a catheter having a deflectable end region;

an end effector adapted to form a needle track at a treatment site in an interior region of the cardiac chamber, the end effector movable between a first position, wherein the end effector is retracted within the end region, and a second position, wherein the end effector is extended beyond a distal endface of the catheter; and means for depositing a bioactive agent in the needle track when the end effector is in the second position *and wherein the catheter has a plurality of lumens, one of which contains the bioactive agent and wherein the catheter has a conductor extending from a proximal end of the catheter to an electrode which is distal to the deflectable end region*.

9. The apparatus of claim 8 wherein the end effector comprises a non-curing sharpened tip.

10. The apparatus of claim 8 wherein the end effector further comprises an electrode adapted to deliver RF energy to the treatment site.

11. The apparatus of claim 10 wherein the bioactive agent is a fluid and the means for depositing comprises supplies the fluid to the end effector under pressure.

12. The apparatus of claim 8 wherein bioactive agent has a pellet form and the means for depositing the bioactive agent comprises a push rod.

13. A method of treating an interior region of a cardiac chamber *the method* comprising:

providing apparatus having a catheter adapted for insertion into a cardiac chamber, the catheter having a deflectable end region including an end effector adapted to form a needle track at a treatment site in an interior region of the cardiac chamber, *wherein the catheter has a plurality of lumens, one of which contains a bioactive agent, wherein the catheter has a conductor extending from the proximal end of the catheter to the distal end of the catheter and the conductor is coupled to the end effector*;

inserting the apparatus within a cardiac chamber;

deflecting the end region to dispose the end effector at a selected orientation relative to an endocardial surface;

actuating the end effector to form a needle track in an interior region of the cardiac chamber at a treatment site; and delivering a controlled amount of [a] *the* bioactive agent at the treatment site, *wherein the needle track, after the delivering, is substantially closed onto the bioactive agent*.

14. The method of claim 13 further comprising delivering RF energy to the treatment site to create a controlled depth of necrosis at the treatment site.

15. The method of claim 13 wherein delivering a controlled amount of a bioactive agent at the treatment site further comprises injecting the bioactive agent under pressure sufficient to form a pocket of bioactive agent in the tissue.

16. The method of claim 13 wherein delivering a controlled amount of a bioactive agent at the treatment site further comprises injecting a pellet comprising a bioactive agent.

17. The method as defined in claim 13 wherein the end effector further comprises a plurality of fine wires, the fine wires movable between a retracted position and an extended position, the method further comprising extending the plurality of fine wires to form a matrix of additional needle tracks at the treatment site.

18. The method as defined in claim 13 further comprising, following delivering a controlled amount of a bioactive agent at the treatment site:

translating the end region to relocate the end effector; and repeating actuation of the end effector.

*19. An apparatus, comprising:*

*a catheter configured for percutaneous insertion into a cardiac tissue, the catheter having a proximal region, a steerable distal region, and a lumen extending from the proximal region to the steerable distal region;*

*a needle disposed distal to the steerable distal region and movable between a first position, wherein the needle is retracted within the distal region, and a second position, wherein the needle is extended beyond the distal region; and*

*a controller coupled near the proximal region and having a source of a bioactive agent, wherein the controller mechanically measures a controlled amount of the bioactive agent, and wherein the bioactive agent is passed through the lumen, in fluid communication with the needle, for delivery into the cardiac tissue, wherein the needle further comprises a means for depositing the controlled amount of the bioactive agent into the cardiac tissue, and wherein the catheter has a plurality of lumens, one of which contains the bioactive agent and wherein the catheter has a conductor extending from a proximal end of the catheter to an electrode which is distal to the steerable distal region.*

*20. The apparatus of claim 19, wherein the bioactive agent has a pellet form.*

*21. The apparatus of claim 19, wherein the bioactive agent has a fluid form.*

*22. The apparatus of claim 19, wherein the controller releases a plurality of discrete units of the bioactive agent through the lumen of the needle.*

*23. The apparatus of claim 22, wherein the plurality of discrete units of the bioactive agent comprises a predetermined amount of the bioactive agent.*

*24. The apparatus of claim 19, wherein the needle further comprises an electrode adapted to delivery RF energy to the cardiac tissue.*

*25. The apparatus of claim 19, wherein the controller comprises a chamber adapted to contain the bioactive agent.*

*26. The apparatus of claim 19, further comprising a mechanical driver coupled near the proximal region, wherein the mechanical driver retracts and extends the needle a controlled depth into the cardiac tissue.*

*27. An apparatus, comprising:*

*a catheter configured for percutaneous insertion into a cardiac tissue, the catheter having a proximal region, a steerable distal region, and a lumen extending from the proximal region to the steerable distal region;*

*a needle disposed distal to the steerable distal region and movable between a first position, wherein the needle is retracted within the distal region, and a second position, wherein the needle is extended beyond the distal region; and*

*a controller coupled near the proximal region and having a source of a bioactive agent, wherein the controller passes a predetermined amount of the bioactive agent through the lumen, in fluid communication with the needle, for delivery into the cardiac tissue, wherein the needle further comprises a means for depositing the predetermined amount of the bioactive agent into the cardiac tissue, and wherein the catheter has a plurality of lumens, one of which contains the bioactive agent and wherein the catheter has a conductor extending from a proximal end of the catheter to an electrode which is distal to the steerable distal region.*

*28. The apparatus of claim 27, wherein the bioactive agent has a pellet form.*

*29. The apparatus of claim 27, wherein the bioactive agent has a fluid form.*

*30. The apparatus of claim 27, wherein the controller mechanically measures a controlled amount of the bioactive agent.*

*31. The apparatus of claim 27, wherein the needle further comprises an electrode adapted to delivery RF energy to the cardiac tissue.*

*32. The apparatus of claim 27, further comprising a mechanical driver coupled near the proximal region, wherein the mechanical driver retracts and extends the needle a controlled depth into the cardiac tissue.*

*33. A method for delivering a bioactive agent to a patient's cardiac tissue, the method comprising:*

*providing a catheter adapted for percutaneous insertion into the cardiac tissue, the catheter having a steerable end region and a hollow needle adapted to deliver discrete units of a bioactive agent having a predetermined dosage and a push rod to push the discrete units, wherein the catheter has a plurality of lumens, one of which contains the bioactive agent, wherein the catheter has a conductor extending from the proximal end of the catheter to the distal end of the catheter and the conductor is coupled to an electrode which is distal to the steerable end region;*

*inserting the catheter within the cardiac tissue;*

*steering the steerable end region to dispose the hollow needle at a selected orientation relative to an interior surface of the cardiac tissue; and*

*delivering and mechanically measuring a controlled amount of the bioactive agent to the cardiac tissue.*

*34. The method of claim 33, further comprising delivering a plurality of discrete units of the bioactive agent to the cardiac tissue.*

*35. The method of claim 33 wherein delivering comprises injecting the bioactive agent under pressure sufficient to form a pocket of the bioactive agent in the cardiac tissue.*

*36. The method of claim 33 wherein delivering comprises injecting the bioactive agent in a pellet form.*

*37. The method of claim 33 wherein delivering comprises injecting the bioactive agent in a fluid form.*

*38. The method of claim 33, further comprising delivering RF energy to the cardiac tissue.*

*39. The method of claim 33, further comprising mechanically retracting and extending the needle a controlled depth into the cardiac tissue.*

*40. A method for delivering a bioactive agent to a patient's cardiac tissue, the method comprising:*

*providing a catheter adapted for percutaneous insertion into the cardiac tissue, the catheter having a steerable end region and a needle adapted to deliver discrete units of a bioactive agent having a predetermined dosage, wherein the catheter has a plurality of lumens, one of which contains the discrete units, and a push rod to push the discrete units, wherein the catheter has a conductor extending from the proximal end of the catheter to the distal end of the catheter and the conductor is coupled to an electrode coupled to the needle near the steerable end region;*

*inserting the catheter within the cardiac tissue;*

*steering the steerable end region to dispose the needle at a selected orientation relative to an interior surface of the cardiac tissue; and*

*mechanically delivering the predetermined dosage of the bioactive agent through the needle into the cardiac tissue using the push rod.*

*41. The method of claim 40, further comprising delivering a plurality of discrete units of the bioactive agent to the treatment site.*

*42. The method of claim 41, further comprising mechanically measuring a controlled amount of the bioactive agent.*

*43. The method of claim 41 wherein delivering comprises injecting the bioactive agent under pressure sufficient to form a pocket of the bioactive agent in the cardiac tissue.*

*44. The method of claim 41 wherein delivering comprises injecting the bioactive agent in a pellet form.*

*45. The method of claim 41 wherein delivering comprises injecting the bioactive agent in a fluid form.*

*46. The method of claim 41, further comprising delivering RF energy to the cardiac tissue.*

*47. The method of claim 40, further comprising mechanically driving the needle to control a penetration depth of the needle into the cardiac tissue.*

*48. An apparatus for delivering a bioactive agent to a patient's cardiac tissue, the apparatus comprising:*

*means for providing a catheter adapted for percutaneous insertion into the cardiac tissue, the catheter having a steerable end region and a hollow needle adapted to deliver discrete units of a bioactive agent having a predetermined dosage, wherein the catheter has a plurality of lumens, one of which contains the discrete units, and a push rod to push the discrete units, wherein the catheter has a conductor extending from the proximal end of the catheter to the distal end of the catheter and the conductor is coupled to an electrode which is distal to the steerable end region;*

*means for inserting the catheter within the cardiac tissue;*

*means for steering the steerable end region to dispose the hollow needle at a selected orientation relative to an interior surface of the cardiac tissue; and*

*means for delivering and mechanically measuring a controlled amount of the bioactive agent.*

*49. An apparatus for delivering a bioactive agent to a patient's cardiac tissue, the apparatus comprising:*

*means for providing a catheter adapted for percutaneous insertion into the cardiac tissue, the catheter having a steerable end region and a needle adapted to deliver discrete units of a bioactive agent having a predetermined dosage, wherein the catheter has a plurality of lumens, one of which contains the discrete units, and a push rod to push the discrete units, wherein the catheter has a conductor extending from the proximal end of the catheter to the distal end of the catheter and the conductor is coupled to an electrode which is distal to the steerable end region;*

*means for inserting the catheter within the cardiac tissue;*

*means for steering the steerable end region to dispose the needle at a selected orientation relative to an interior surface of the cardiac tissue; and*

*means for mechanically delivering the predetermined dosage of the bioactive agent through the needle into the cardiac tissue.*

*50. An apparatus, comprising:*

*a catheter configured for percutaneous insertion into a cardiac tissue, the catheter having a proximal region, a steerable distal region which is deflectable, and a lumen extending from the proximal region to the steerable distal region;*

*a needle disposed distal to the steerable distal region and movable between a first position, wherein the needle is retracted within the distal region, and a second position, wherein the needle is extended beyond the distal region and wherein the needle is deflectable within the steerable distal region; and*

*a controller coupled near the proximal region and having a source of a bioactive agent in the form of discrete units, wherein the controller passes a predetermined amount of the bioactive agent through the lumen, in fluid communication with the needle, for delivery into the cardiac tissue, wherein the needle further comprises a means for depositing the predetermined amount of the bioactive agent into the cardiac tissue, and wherein the catheter has a plurality of lumens, one of which contains the bioactive agent and wherein the catheter has a conductor extending from a proximal end of the catheter to an electrode which is distal to the steerable distal region.*

*51. The apparatus of claim 50, wherein the bioactive agent has a pellet form.*

*52. A method for delivering a bioactive agent to a patient's cardiac tissue, the method comprising:*

*providing a catheter adapted for percutaneous insertion into the cardiac tissue, the catheter having a steerable end region and a hollow needle adapted to deliver granules of a bioactive agent having a predetermined dosage, wherein the catheter has a plurality of lumens, one of which contains the granules, and a push rod to push the granules, wherein the catheter has a plurality of lumens, one of which contains the bioactive agent, wherein the catheter has a conductor extending from the proximal end of the catheter to the distal end of the catheter and the conductor is coupled to an electrode which is distal to the steerable end region;*

*inserting the catheter within the cardiac tissue;*

*steering the steerable end region to dispose the hollow needle at a selected orientation relative to an interior surface of the cardiac tissue; and*

*mechanically delivering a controlled amount of the granules using the push rod.*

*53. The method of claim 52, wherein the catheter includes a plurality of granules.*

*54. The method of claim 53, wherein mechanically delivering comprises separating a single granule from the plurality of granules.*

*55. The method of claim 54 additionally comprising inserting a single granule within the cardiac tissue.*

*56. The method of claim 52 additionally comprising inserting at least one granule into the cardiac tissue and wherein the mechanically delivering comprises measuring the controlled amount.*

*57. The method of claim 52, wherein inserting comprises inserting the hollow needle into the cardiac tissue.*

*58. The method of claim 57, wherein a portion of the catheter allows only the hollow needle to insert into the cardiac tissue.*

*59. The method of claim 57, wherein a path into the cardiac tissue is created by inserting the hollow needle.*

*60. The method of claim 59, wherein the path substantially closes after the hollow needle is withdrawn from the cardiac tissue such that the granule is in complete contact with the cardiac tissue.*

* * * * *